United States Patent [19]

Nishizawa

[11] Patent Number: 5,516,667
[45] Date of Patent: May 14, 1996

[54] CHILLING-RESISTANT PLANTS AND THEIR PRODUCTION

[75] Inventor: Osamu Nishizawa, Shioya, Japan

[73] Assignee: Kirin Beer Kabushiki Kaisha, Tokyo, Japan

[21] Appl. No.: 87,732

[22] PCT Filed: Jan. 14, 1992

[86] PCT No.: PCT/JP92/00024

§ 371 Date: Jul. 16, 1993

§ 102(e) Date: Jul. 16, 1993

[87] PCT Pub. No.: WO92/13082

PCT Pub. Date: Aug. 6, 1992

[30] Foreign Application Priority Data

Jan. 16, 1991 [JP] Japan .................................. 3-015883
Oct. 4, 1991 [JP] Japan .................................. 3-283807

[51] Int. Cl.[6] .............................. A01H 1/04; A01H 5/00; C12N 15/00
[52] U.S. Cl. ..................... 435/172.3; 435/69.1; 435/134; 435/193; 800/205; 800/DIG. 15; 800/DIG. 23
[58] Field of Search ........................... 800/205, DIG. 15, 800/DIG. 23; 435/172.3, 240.49, 240.51, 69.1, 134, 193

[56] References Cited

U.S. PATENT DOCUMENTS 5,210,189  5/1993  Murata .................................. 536/23.2

FOREIGN PATENT DOCUMENTS 0255378   2/1988  WIPO.
WO90/12084  10/1990  WIPO.
WO91/13972   9/1991  WIPO.

OTHER PUBLICATIONS

Lyons "Chilling Injury in Plants", *Ann. Rev. Plant Physiol.*, 24:445–466 (1973).
Murata et al. "Lipids Of Blue–Green Algae", *Biochemistry of Plants (Lipids: Structure and Function)*, 9:315–347 (1987).
Santaren et al. "Thermal And $^{13}$C–NMR Study Of The Dynamic Structure Of 1–Palmitoyl–2–Oleyl . . . ", *Biochimica et Biophysica Acta.*, 687:231–237 (1982).
Phillips et al. "The Inter– And Intra–Molecular Mixing Of Hydrocarbon Chains In Lecithin/Water Systems", *Chem. Phys. Lipids*, 8:127–133 (1972).
Roughan "Phosphatidylglycerol and Chilling Sensitivity in Plants", *Plant Physiology*, 77:740–746 (1985).
Murata et al. "Lipids In Relation To Chilling Sensitivity Of Plants", *Chilling Injury of Horticultural Crops*, Chapter 11:181–199 (1990).
Sparace et al. "Phosphatidylglycerol Synthesis in Spinach Chloroplasts: Characterization of the Newly Synthesized Molecule", *Plany Physiology*, 70:1260–1264 (1982).
Bertrams et al. "Positional Specificity and Fatty Acid Selectivity of Purified sn–Glycerol 3–Phosphate Acyltransferases from Chloroplasts[1]", *Plant Physiology*, 68:653–657 (1981).

Nishida et al. "Purification of Isomeric Forms of Acyl–[Acyl–Carrier–Protein]: Glycerol–3–Phosphate Acyltransferase from Greening Squash Cotyledons", *Plant Cell Physiology*, 28(6):1071–1079 (1987).
Frentzen et al. "Properties of the Plastidial Acyl–(Acyl–Carrier–Protein): Glycerol–3–Phosphate Acyltransferase from the Chilling–Sensitive . . . ", *Plant Cell Physiology*, 28(7):1195–1201 (1987).
Bishop et al. "Thermal Properties of 1–Hexadecanoyl–2–Trans–3–Hexadecenoyl Phosphatidylglycerol", *Phytochemistry*, 26, 11:3065–3067 (1987).
Van der Broeck et al. "Targeting of a Foreign Protein to Chloroplasts by Fusion to the Transit Peptide From the Small Subunit of Ribulose 1,5–Bisphosphate Carboxylase", *Nature*, 313:358–363 (1985).
Nishida et al. "The geonomic gene and cDNA for the plastidial glycerol–3–phosphate acyltransferase of Arabidopsis", *Mol. Biology and Tech.*, 462–467 (1990).
Murata "Molecular species composition of phosphatidylglycerols from chilling–sensitive . . . ", *Plant Cell Physio . . .*, 24(1):81–86 (1983).
Ishizaki et al. "Cloning and nucleotide sequence of cDNA for the plastic glycerol–3–phosphate . . . ", *Febs Ltrs*, 238(2):424–430, (1988).
Weber et al. "Purification and cDNA sequencing of an oleate–selective acyl–ACP:sn–glycerol . . . ", *Plant Molecular Biology*, 17:1067–1076 (1991).
Frentzen et al. "Specificities and selectivities of glycerol 3–phosphate acyltransferase and monoacylglycerol . . . ", *Eur. J. Biochem.*, 129(3):629–6363 (1983).
Nishizawa et al. "Expression of squash glyderol–3–phosphate acyltransferase gene in transgenic tobacco plants", *Mol. Biol. & Biotech.*, 465–467.
Cronan et al. *Biological Abstracts*, 84:8924 (1987).

(List continued on next page.)

*Primary Examiner*—David T. Fox
*Assistant Examiner*—E. F. McElwain
*Attorney, Agent, or Firm*—Foley & Lardner

[57] ABSTRACT

The present invention relates to the genetic engineering of higher plants to confer chilling resistance. Provided is a higher plant which contains more unsaturated fatty acids in membrane lipids than are inherent to that plant species, and a process for producing the same. A preferred embodiment of such plant is a transgenic plant expressing a polypeptide with a glycerol 3-phosphate acyltransferase activity that has a higher substrate selectivity for oleoyl-(acyl-carrier-protein) (oleoyl-ACP) than for palmitoyl-(acyl-carrier-protein) (palmitoyl-ACP). In another aspect, there are provided higher plants with a lowered critical temperature for chilling injury, and a process to produce the same. A preferred embodiment of such plant is a transgenic plant whose phosphatidylglycerol contains reduced amount of saturated molecular species due to the expression of a polypeptide with a glycerol 3-phosphate acyltransferase activity that has a higher substrate selectivity for oleoyl-ACP than for palmitoyl-ACP.

12 Claims, 3 Drawing Sheets

OTHER PUBLICATIONS

Wada et al. "Enhancement of chilling tolerance of a cyanobacterium by genetic manipulation . . . ", *Nature*, 347:200–203 (1990).

Bafor et al. "Properties of the Glycerol Acylating Enzymes in Microsomal Preparations from the Developing . . . ", *JAOCS*, 67(4):217–225 (1990).

Wolter et al. *Biological Abstracts* BR42:6024.

Murata (Oct. 1991) International Society for Plant Molecular Biology, 3rd Intl Congress, Abstracts #55.

Goodwin et al (1983) Introduction to Plant Biochemistry, Pergamon Press, Oxford, p. 45.

Murata et al (1992, Apr.) Nature 356:710–713.

Axtell (1981) Breeding for Improved Nutritional Quality, In: Plant Breeding II (Frey, ed.) Iowa State Univ. Press pp. 365–415.

FIG. 3(A) pBI121

Before

After

FIG. 3(C) Arabidopsis ATase

Before

After

CHILLING-RESISTANT PLANTS AND THEIR PRODUCTION

FIELD OF THE INVENTION

The present invention relates to a plant with an altered fatty acid composition of lipids, more specifically, a plant made resistant to chilling injury by altering the fatty acid composition of its lipids, and a process to produce such plant.

BACKGROUND OF THE INVENTION

Low temperature injury of higher plants is largely categorized into two different types. One is the injury caused by temperatures at or below 0° C. and is called "freezing injury". The other, which is the subject matter of the present invention, is called "chilling injury" and is totally different from freezing injury. Most tropical and subtropical plants suffer chilling injury at temperatures in the range of 5° to 15° C., which injury damages the tissue(s) of whole and/or a part of the plants leading to a variety of physiological dysfunctions and ultimately to death in the severest cases.

Plants susceptible to chilling injury are called "chilling-sensitive" plants and include many important crops such as rice, maize, yam, sweet potato, cucumber, green pepper, eggplant, squash, banana, melon, kalanchoe, cyclamen, lily, rose, castor bean, sponge cucumber and tobacco. These plants suffer a variety of injuries, such as the inhibition of germination and growth, tissue necrosis as well as the death of the whole plant, at temperatures between 5° and 15° C., in most cases at around 10° C., and thus are prone to damage by cold weather and frost. Furthermore, fruits, vegetables, and the like harvested from chilling-sensitive plants cannot tolerate low temperature storage (as illustrated by the black decaying spots that quickly appear on bananas when taken out of a refrigerator) making it difficult to store these harvests for a long period after the harvest.

Most plants of temperate origin, on the other hand, are chilling-resistant and are not injured even by a low temperature of around 0° C. Chilling-resistant crop plants include wheat, barley, spinach, lettuce, radish, pea, leek, and cabbage. Wild weeds such as dandelion and Arabidopsis are also chilling-resistant.

Chilling injury is significantly related to the fluidity of membrane lipids that constitute biomembranes. Biomembranes are one of basic organizing units of living cells. They define the inside and outside of cells as the cell membrane and in eukaryotic cells also organize a variety of membrane structures (cell organelles) to partition the cell into several functional units. Biomembranes are not mere physical barriers against high molecular weight substances and low molecular weight electrolytes; the function of proteins associated with the membranes allow the selective permeation, and/or the active transport against concentration gradient, of particular substances. In this way biomembranes keep the micro-environment of cytoplasm and cell organelles in a suitable condition for their purpose. Some biochemical processes, such as energy production by respiration and photosynthesis, require a specific concentration gradient of particular substances across biomembranes. In photosynthesis, the energy of light generates a hydrogen ion gradient potential across the thylakoid membrane within chloroplasts, which potential energy is then convened to ATP, a high-energy compound utilized by living cells, by proteins in the thylakoid membrane. Accordingly, if biomembranes fail to function as a barrier as described above, it will disturb not only the micro-environment of cells but impair these cellular functions based on a concentration gradient, leading to serious dysfunctions of living cells.

The membrane lipids that constitute biomembranes are mainly phospholipids and, in the case of chloroplasts, glycerolipids. Phospholipids are 1,2-di long-chain alkyl (fatty acyl) esters of glycerol with a polar group bonded at the 3 position as a phosphoester. They are amphipathic compounds having both a hydrophilic portion (the polar group) and a hydrophobic portion (the fatty acyl groups) within one molecule and therefore form a lipid bilayer with the hydrophobic portions inside and the hydrophilic portions on the surface when dispersed in an aqueous solution. This lipid bilayer is the basic structure of biomembranes which "buries" a variety of proteins inside and/or on its surface. Under physiological conditions, the lipid bilayer is in the liquid-crystalline phase in which the inside of the bilayer retains a high fluidity, allowing free horizontal dispersion and rotation of protein and lipid molecules within the membrane. This fluidity of biomembranes is essential for cellular functions (Darnell, J. et al, *Molecular cell biology*, Scientific American Books, 1986).

When the temperature of a simple lipid bilayer in the liquid-crystalline phase is lowered to a certain temperature called the phase transition temperature (Tc), the bilayer undergoes a phase transition to the gel phase in which the inside of the membrane has less fluidity. In the case of biomembranes, which consist of different types of lipids, some lipids with a high Tc begin to form gel phase domains at a certain temperature while other lipids with a lower Tc are still in the liquid-crystalline phase, resulting in the phase separation, in which both the liquid-crystalline and gel phases co-exist. In a phase separated state, biomembranes become leaky and no more serve as a barrier against low molecular weight electrolytes.

A relationship between chilling injury and the phase transition of membrane lipids was first proposed in early 1970's (Lyons, J. M., *Ann. Rev. Plant Physiol.*, 24:445, 1973). At that time, however, there was no concrete data supporting the existence of the relationship. Later, in a series of experiments using cyanobacteria (blue-green algae) as model organisms, it was shown that the chilling injury of cyanobacteria is the result of irreversible effluent from the cells of electrolytes such as ions following the phase separation of the cell membrane at a chilling temperature (Murata, N. and Nishida, I., in The biochemistry of plants vol. 9 *Lipids: Structure and function*, p.315, Academic Press, Orlando, 1987).

Lipids are generally classified by the polar group (see above for the structure of membrane lipids), since their behavior in column and thin layer chromatographics is largely determined by the polar group. Among one particular class of lipids with the same polar group, there are many different molecules with various combinations of the two fatty acyl groups in the molecule. The term "molecular species" is used to distinguish these molecules. The Tc of each lipid molecular species depends on the polar group as well as the chain length and degree of unsaturation (the number of double bonds) of the fatty acyl groups, and in some instances the environmental salt concentration and such. Among these, the degree of unsaturation of the fatty acyl groups has the largest effect; while a particular molecular species with two saturated fatty acyl groups usually has a Tc above room temperature, introduction of only one double bond into one of the fatty acyl groups results in the decrease of Tc to around 0° C. (Santaten, J. F. et al, *Biochem. Biophys. Acta*, 687:231, 1982). (However, if the double bond is in the trans configuration, the effect on the Tc is very small [Phillips, M. C. et al, *Chem. Phys. Lipids*, 8:127, 1972]. Most double bonds of membrane lipids are in the cis configuration and the trans configuration is relatively rare.) This indicates that a lipid molecular species with at least one double bond in its fatty acyl groups (hereinafter called "unsaturated molecular species") does not undergo phase transition at around 10° C., the critical temperature for chilling injury. Consequently, only those lipid molecules with two saturated fatty acyl groups (hereinafter called "saturated molecular species") could induce the phase separation of biomembranes which is considered to be the primary event in chilling injury.

Membrane lipids have been extracted from several chilling-sensitive and resistant plants, separated according to the polar group, and their fatty acid and molecular species compositions analyzed. The results showed that only phosphatidylglycerol (PG) contains a significant amount of saturated molecular species among plant membrane lipids and that the content of saturated molecules in PG is high (30–70 %) in chilling-sensitive plants and low (<20 %) in chilling-resistant plants (Murata, N., *Plant Cell Physiol*, 24:81, 1983; Roughan, P. G., *Plant Physiol.*, 77:740, 1985). Since PG is a major component of plastid (chloroplast, chromoplast) biomembranes, this correlation between the PG molecular species composition and chilling sensitivity strongly suggests that the primary event in the chilling injury of higher plants is the phase separation of plastid biomembranes induced by the phase transition of PG (Murata, N. and Nishida, I., in *Chilling injury of horticultural crops*, p.181, CRC Press, Boca Raton, 1990).

PG is localized in plastids and, in the case of green leaves, synthesized mainly in chloroplasts (Sparace, S. A. and Mudd, J. B., *Plant Physiol.*, 70:1260, 1982). Its biosynthesis follows the steps shown below.

1. Transfer of a fatty acyl group to the sn-1 position of glycerol 3-phosphate.
2. Transfer of another fatty acyl group to the sn-2 position.
3. Esterification of glycerol to the 3-phosphate group.
4. Desaturation of fatty acyl groups on the molecule.

Fatty acids are exclusively synthesized in chloroplasts. The synthesized fatty acids are supplied to steps 1 and 2 of PG synthesis as acyl-ACP complexes wherein the fatty acids are bound to a protein called acyl carrier protein (ACP). Most of the fatty acids synthesized in chloroplasts are palmitic acid (saturated C-16 acid, hereinafter designated as 16:0) and oleic acid (mono-unsaturated C-18 acid, hereinafter designated as 18:1).

Step 1 of the above scheme is catalyzed by acyl-ACP:glycerol 3-phosphate acyltransferase (EC 2.3.1.15) (hereinafter called ATase). This enzyme is a soluble enzyme in chloroplast stroma. It has been partially purified from spinach and pea (Bertrams, M. and Heinz, E., Plant Physiol., 68:653, 1981) and purified to homogeneity from squash (Nishida, I. et al, *Plant Cell Physiol.*, 28:1071, 1987). It is encoded by a nuclear gene, which has been cloned from squash, Arabidopsis and recently from pea (Ishizaki, O. et al, *FEBS Lett.*, 238:424, 1988; Nishida, I. et al., in *Plant lipid biochemistry, structure and utilization*, Portland Press, London, 1990; Weber, S. et al, *Plant Molec. Biol.*, 17:1067, 1991). ATases from different sources differ in selectivity for the substrate, acyl-ACP. While ATases from spinach, pea and Arabidopsis, which are chilling-resistant, have a high selectivity for 18:1-ACP, ATase from squash, a chilling-sensitive plant, equally utilizes both 18:1-ACP and 16:0-ACP (Frentzen, M. et al, *Eur. J. Biochem.*, 129:629, 1983; Frentzen, M. et al., *Plant Cell Physiol*, 28:1195, 1988).

The enzyme that catalyzes step 2 of the above scheme is a membrane-bound enzyme of chloroplast envelope and utilizes only 16:0-ACP (Frentzen, M. et al, *Eur. J. Biochem.*, 129:629, 1983). In a number of plant species called 16:3 plants, the intermediate product of steps 1 and 2, phosphatidic acid (1,2-diacylglycerol 3-phosphate), is also an intermediate compound for the biosynthesis of glycerolipids (mono- and digalactosyldiacylglycerols and sulfoquinovosyl-diacylglycerol) synthesized in chloroplasts. Steps 1 and 2 are therefore common to the lipid biosynthesis in chloroplasts of the 16:3 plants.

Very little is known about the enzymes for steps 3 and 4 of PG biosynthesis. However, it is well known that the desaturation of fatty acyl groups in PG is asymmetric. At the sn-1 position, most of 18:1 is further desaturated to have two or three double bonds while 16:0 is not desaturated. At the sn-2 position, some of the bound 16:0 is desaturated to 3-trans-hexadecenoic acid (hereinafter designated as 16:1t) but no cis-double bond is introduced. Since a trans-double bond is much less effective in decreasing the phase transition temperature, the conversion of 16:0 to 16:1t at tic position 2 of PG would decrease the Tc by only about 10° C., so that the Tc is still higher than the critical temperature for chilling injury (Bishop, D. G. and Kenrick, J. R., *Phytochemistry*, 26:3065, 1987). PG molecular species with 16:1t are accordingly included within saturated molecular species hereinafter. Because no cis-double bond is introduced in the fatty acyl group at position 2, the fatty acyl group at the position 1 is very important in determining the content of saturated molecular species.

Chilling-sensitive crop plants suffer significant disadvantages in low-temperature tolerance and long-term post-harvest storage as described above. Nevertheless, many of chilling-sensitive crops are very important and indispensable for agricultural production; for example, rice and maize are the main cereal crops in many parts of the world. An improvement in the chilling resistance of these crops would make it easier to grow them in a chilling environment and/or to store their harvest for a long period. In the case of ornamental flowers and vegetables grown in a greenhouse due to their chilling-sensitivity, improvement of chilling resistance would make the greenhouse unnecessary or save the heating expense to a great extent. Furthermore, the improvement might expand the area where the crop is grown, since temperature is often the main factor to define the borders of crop development.

There is thus a significant demand for chilling resistant plants and chilling resistance has been one of the major goals of crop breeding. However, conventional crossing breeding is limited in genetic sources for this purpose, because one can cross the crop only within the same species. Recent progress in genetic engineering of higher plants has made it possible to introduce genetic information into crops from an unlimited range of genetic sources. The application of genetic engineering to providing chilling-resistance would therefore be invaluable.

As already described, the primary event in the chilling injury of higher plants is the phase separation of plastidial membranes, and the plastidial membranes of chilling-sensitive plants contain a higher mount of the saturated PG molecular species considered to induce the phase separation. It was thus suggested that it might be possible to increase the chilling resistance of chilling-sensitive plants by changing the fatty acid composition of their PG to decrease the content of saturated molecular species (Murata, N., *Plant Cell Physiol*, 24:81, 1983). However, this was only a hypothesis and, to date, there has been no report of any method to change the fatty acid composition of cellular lipids nor any report of a plant with an altered fatty acid composition.

SUMMARY OF THE INVENTION

The present invention provides novel methods for increasing the unsaturated fatty acid content of membrane lipids, particularly phosphatidylglycerol (PG), in higher plant. Briefly summerized, these methods involve introducing and expressing a DNA sequence encoding a polypeptide with a glycerol 3-phosphate acyltransferase (ATase) activity having a higher substrate selectivity for oleoyl-(acyl-carrier-protein) (18:1-ACP) than for palmitoyl-(acyl-carrier-protein) (16:0-ACP).

The present invention also provides for higher plants which contain more unsaturated fatty acids in membrane lipids than are inherent to plants of the species. A preferred embodiment of such a plant is a transgenic plant expressing a polypeptide with a glycerol 3-phosphate acyltransferase activity that has a higher substrate selectivity for oleoyl-(acyl-carrier-protein) than for palmitoyl-(acyl-carrier-protein).

As previously noted, ATase catalyzes the first step of lipid biosynthesis in chloroplasts and ATases from different plant species exhibit different substrate selectivity for acyl-ACPs. ATases from chilling-resistant plants such as spinach, pea and Arabidopsis have a high selectivity for 18:1-ACP, and ATases from chilling-sensitive plants such as squash equally utilize both 18:1-ACP and 16:0-ACP.

DNA sequences for use in the present invention and encoding an ATase that having a higher substrate selectivity for 18:1-ACP can be any of the DNA sequences encoding an ATase of a chilling-resistant plant and DNA sequences encoding ATases from organisms other than higher plants. Preferably, a DNA sequence encoding an ATase of a chilling-resistant plant, more preferably the ATase of spinach, pea or Arabidopsis, is employed. The expression of the exgenous DNA sequence and the production thereby of the ATase can be accomplished by providing the DNA sequence with an appropriate combinations of expression regulatory sequences (promoter, terminator, and such) and a sequence encoding a transit peptide necessary, for the transport of proteins into chloroplasts. The DNA construct can be introduced into plant genome by any of the conventional techniques known to those skilled in art and suitable for use with the target plant.

According to the present invention, introduction and expression in a higher plant of an exogenous DNA sequence encoding an ATase that has a higher substrate selectivity for 18:1-ACP increases the unsaturated fatty acid content in membrane lipids of the plant. Of particular significance to practice of the invention is the increases in the unsaturated fatty acid content of PG resulting in a prominent decrease of saturated PG molecular species. As already described, saturated PG molecular species induce the phase separation of plastidial biomembranes, and it has been shown that resistance to chilling injury is inversely correlated to the content of saturated PG molecular species within a particular plant species.

Consequently, in another aspect of the present invention, there is provided a process to lower the critical temperature for chilling injury of a higher plant species that is inherently injured by a low temperature above 0° C. (a chilling-sensitive plant) by decreasing the content of saturated phosphatidylglycerol molecular species.

Yet another aspect of the present invention provides higher plants with an improved resistance to chilling injury. In other words, the present invention provides inherently chilling-sensitive species of higher plants with a lowered critical temperature for chilling injury. A preferred embodiment of such plant is a transgenic plant whose phosphatidylglycerol contains a reduced amount of saturated molecular species due to the expression of a polypeptide with a glycerol 3-phosphate acyltransferase activity that has a higher substrate selectivity for oleoyl-(acyl-carrier-protein) than for palmitoyl-(acyl-camer-protein).

BRIEF DESCRIPTION OF THE DRAWINGS

FIGS. 3A–3D show the effect of a chilling treatment on transgenic tobacco plants at the whole plant level. Upper and lower plates are control pBI-121 transformed tobacco plants and the Arabidopsis ATase cDNA transgenic plants, respectively, before (left) and after (right) the chilling treatment.

DETAILED DESCRIPTION OF THE INVENTION

Figure 1:
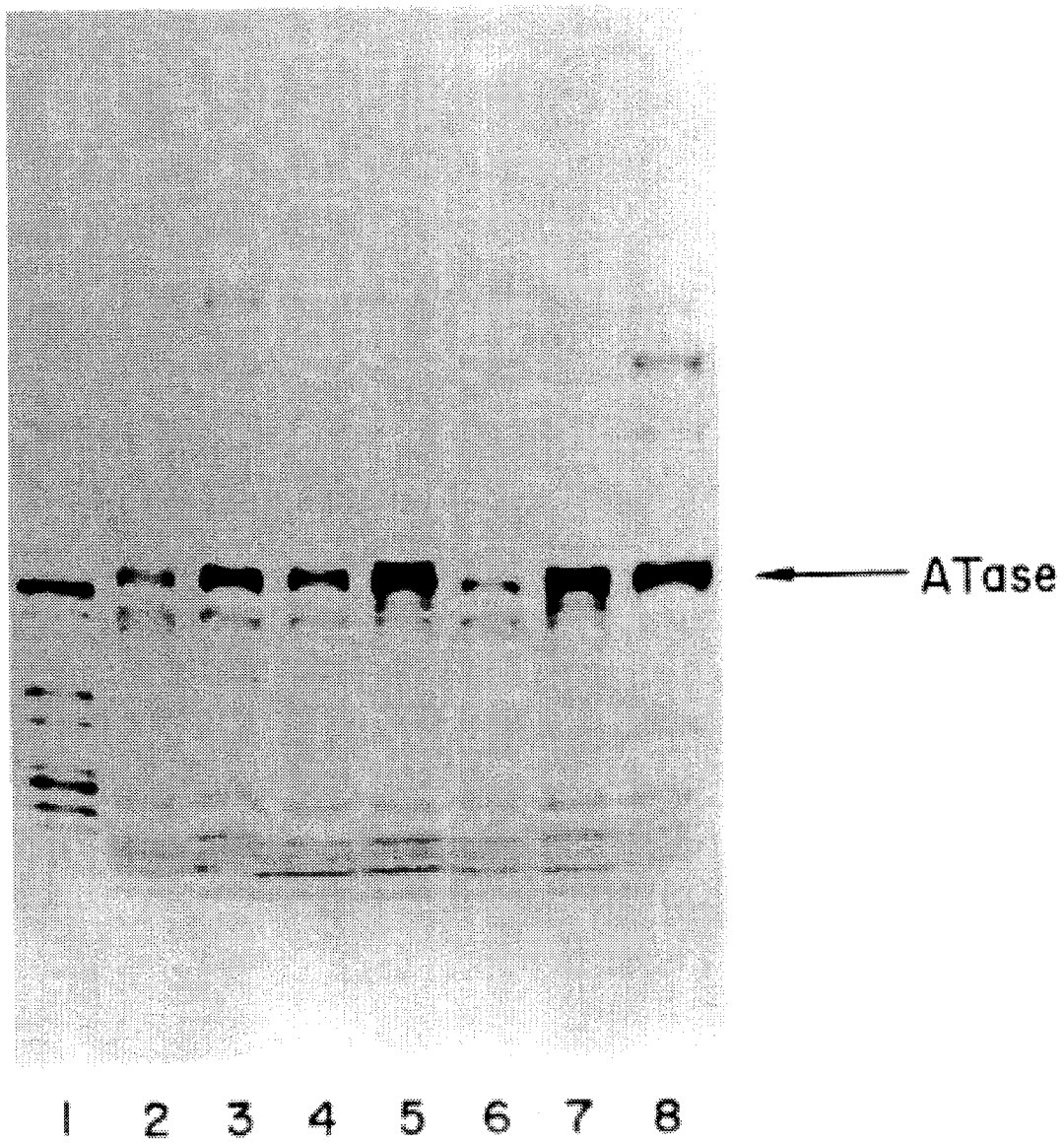
FIG. 1 shows a result of Western blotting analysis of Arabidopsis ATase transgenic tobacco plants using an anti-Arabidopsis ATase antibody. Lane 1 contains 50 ng of an Arabidopsis ATase preparation expressed in $E.$ $coli.$ Lane 2 contains 10 µg of the total chloroplast protein of a non-transformed control plant. Lanes 3–7 contain 10 µg each of the total chloroplast protein from transgenic plants No. 1–5, respectively. Lane 8 contains 10 µg of the total leaf protein from transgenic plant No. 1.

In general, when a DNA sequence is to be expressed to produce the polypeptide it encodes, expression regulatory sequences are essential in addition to the coding sequence corresponding to the polypeptide. Particularly important are a promoter sequence upstream and polyadenylation signals downstream of the coding sequence. In the present invention, any appropriate combination of promoters and polyadenylation signals that are known to function in plant cells can be employed; e.g. cauliflower mosaic virus 35S promoter, nopaline synthase promoter, and ribulose bisphosphate carboxylase/oxygenase small subunit promoter, as well as nopaline synthase polyadenylation signals and octopine synthase polyadenylation signals. Furthermore, if the expressed polypeptide is to be transported into a particular compartment of the cell, such as the chloroplasts, a transit or leader peptide sequence is necessary at the N-terminus of the polypeptide. Accordingly, in the present invention, "DNA sequence encoding ATase (or a polypeptide with an ATase activity)" shall not be limited to the coding region but include the expression regulatory sequences and/or a DNA sequence encoding the transit peptide.

A DNA sequence encoding a polypeptide with an ATase activity having a higher substrate selectivity for 18:1-ACP than for 16:0-ACP suitable for use in the present invention is preferably one encoding an ATase from a chilling-resistant plant, particularly spinach, pea, or Arabidopsis. Such DNA sequences can be obtained in whole or part by chemical synthesis; alternatively and more preferably, the DNA sequence can be obtained by cloning a cDNA or genomic DNA encoding the ATase from chilling-resistant plants. In the following examples, a cDNA sequence encoding the ATase from *Arabidopsis thaliana* (Nishida, I. et al, in *Plant lipid biochemistry, structure and utilization,* Portland Press, London, 1990) was used. DNA sequences that can be used in this invention, however, are not limited to this particular cDNA sequence.

The nucleotide sequence of the cDNA encoding Arabidopsis ATase is shown in SEQ ID NO:1. The isolation of this cDNA itself is not a part of the present invention; nevertheless, a detailed process for its isolation is described below in Experimental examples 1 and 2. Briefly, a genomic clone encoding Arabidopsis ATase was obtained from an Arabidopsis genomic library using a cDNA fragment for squash ATase as the probe. This genomic DNA was then used to screen an Arabidopsis cDNA library to obtain the cDNA clone. The Arabidopsis cDNA of SEQ ID NO:1 codes for a polypeptide of 459 amino acids (SEQ ID NO: 2) with a molecular mass of 50,431. The N-terminal 90 amino acid portion of this polypeptide is assumed to be a transit peptide for the transport to chloroplasts which is cleaved off during the transporting process, resulting in a mature enzyme of 369 amino acids. An ATase preparation from *E. coil* expressing this cDNA has a higher substrate selectivity for 18:1 than for 16:0 (Experimental example 3).

When the DNA sequence is a cDNA, appropriate expression regulatory sequences are necessary at upstream and downstream of the cDNA sequence in order to express the cDNA in transgenic plants. When the DNA sequence is a genomic DNA fragment and contains regulatory sequences, the fragment may be used by itself. Furthermore, since the ATase expressed according to this invention is involved in the lipid biosynthesis of chloroplasts, the ATase expressed in the transgenic plants must be transported from the cytoplasm to chloroplasts. Generally, a transit peptide sequence at the N-terminus is necessary to transport a nuclear-encoded protein to chloroplasts (Van den Broeck et al, *Nature*, 313:358, 1985). Because plastidial ATases of higher plants are produced in the cytosol and function in chloroplasts by nature, DNA sequences encoding the ATase from higher plants, be it a cDNA or a genomic DNA fragment, should contain a DNA sequence encoding an amino acid sequence functioning as a transit peptide, as illustrated by the cDNA for Arabidopsis ATase used in the following examples. Nevertheless, if necessary, DNA sequences encoding a known transit peptide, such as that of ribulose bisphosphate carboxylase/oxygenase small subunit, may be employed.

The DNA sequence encoding a polypeptide (SEQ ID Nos: 1 and 2) with an ATase activity having a higher substrate selectivity for 18:1-ACP than for 16:0-ACP according to the present invention can be that encoding an ATase derived from organisms other than higher plants such as bacteria. When such a DNA sequence is used, appropriate expression regulatory sequences and a sequence encoding a transit peptide might be required in an appropriate arrangement upstream and/or downstream of the DNA sequence. Detailed constructions and procedures for generating such arrangements can be found in laboratory manuals such as *Molecular cloning* 2nd ed. (Sambrook et al eds.), Cold Spring Harbor Laboratory Press, New York, 1989, and are obvious to those skilled in the art.

A DNA sequence encoding a polypeptide with an ATase activity having a higher substrate selectivity for 18:1-ACP than for 16:0-ACP for use in the present invention can also be one encoding a derivative of ATases described above. In this context "derivative" means a polypeptide with one or more amino acid substitutions, deletions, insertions or additions to any of the ATases described above, provided the change(s) in the amino acid sequence does not impair the ATase activity nor the substrate selectivity for 18:1.

A list of chilling-sensitive higher plants suitable for practice of the present invention to form transgenic plants includes, but is not limited to, rice, maize, yam, sweet potato, cucumber, green pepper, eggplant, squash, banana, melon, kalanchoe, cyclamen, lily, rose, castor bean, sponge cucumber and tobacco.

Introduction of the DNA sequence into higher plants can be accomplished by any of the established methods for plant transformation, such as the Ti plasmid vector system of Agrobacteirum and electroporation of protoplasts (for example, see *Plant genetic transformation and gene expression; a laboratory manual* (Draper, J. et al. eds.), Blackwell Scientific Publications, 1988), in accordance with the target plant. In general, use of the Ti plasmid vector is preferred for dicotyledonous plants and physical methods such as electroporation are preferred for monocotyledonous plants and dicots that are not susceptible to Agrobacterium infection. Plant materials to be transformed can be any explants such as leaf disks, stem disks, tuber disks, protoplasts, callus, pollens or pollen tubes, in accordance with the transformation protocol.

According to the present invention, introduction and expression in a higher plant of a DNA sequence encoding an ATase that has a higher substrate selectively for 18:1-ACP than for 16:0 increases the unsaturated fatty acid content particularly in PG and also results in a prominent decrease of saturated PG molecular species.

ATase catalyzes the first step of PG biosynthesis; at the same time, however, this step is common to the synthetic pathways of other lipids in chloroplasts of many plants (see Background of the Invention) and thus the reaction products of ATase are utilized not only for PG but various other lipids. Furthermore, since the intrinsic ATase(s) is not eliminated in a transgenic plant expressing a foreign ATase with a different substrate selectivity, the foreign ATase has to compete with the intrinsic ATase. For these reasons it was not possible to predict whether the fatty acid composition of membrane lipids, much less the molecular species composition of PG, would change by expressing the foreign ATase. A prominent decrease of saturated PG molecular species such as observed according to the present invention was totally unexpected.

According to the present invention, it is possible to significantly decrease the amount of unsaturated PG molecular species, the lipid species that gives rise to the phase separation of biomembranes and induce the chilling injury of higher plants. This is the first case of plant genetic engineering for chilling resistance.

The following examples illustrate and describe in more detail the present invention.

Experimental Example 1 Isolation of an Arabidopsis genomic DNA fragment coding for ATase (1) Construction of a genomic DNA library Genomic DNA was prepared from about 10 g (wet weight) of leaves and stems of *Arabidopsis thaliana* Heynhold (Lansberg strain) as described in *Current Protocols in Molecular Biology* (Ausbel, F. M. et al. eds.) vol. 1, pp. 2,3,1–2,3,3, John Wiley and Sons, 1987.

The genomic DNA was partially digested with a restriction enzyme Sau3AI. inserted into the BamHI site of a lambda phage vector λDASH (Stratagene) and packaged in vitro using an in vitro packaging kit (GIGAPACK GOLD; Stratagene) to give a genomic DNA library in λ phage.

(2) Isolation of the ATase genomic DNA fragment

*Escherichia coli* strain P2392 (Stratagene) was infected with the phage library, and three plates (10 cm×14 cm) with 6×10³–6×10⁴ plaques each were screened. The phages were transferred to filters, which were incubated at 68° C. for 2 hours in a hybridization solution containing 5×Denhart's solution [0.1% Ficoll, 0.1% polyvinylpyrrolidone, 0.1% bovine serum albumin], 6×SSC [900 mM NaCl, 90 mM sodium citrate, pH 7.4], 10% dextran sulfate, 0.1% SDS and 100 µg/ml of salmon sperm DNA.

A 1.4 kb cDNA fragment for the ATase of squash (*Cucurbita moschata* Duch) was obtained by excising, with a restriction enzyme EcoRI, from the recombinant plasmid pAT-03 carrying the cDNA for the squash ATase isolated from *E. coil* AT-03 (FERM BP-3094). This cDNA fragment was subjected to nick translation (nick translation kit; Talcam Shuzo) with $^{32}$P-dATP to give a probe with a specific activity of about $10^8$ dpm/µg.

The probe was added to the hybridization solution and the filters were further incubated in this solution at 50° C. for 12 hours. Filters were then washed at 40° C. with 2×SSC and 0.1% SDS solution and subjected to autoradiography to select phages which hybridized strongly to the probe.

The genomic DNA of Arabidopsis was excised from the phage DNA with a restriction enzyme BamHI and subjected to 0.8% agarose gel electrophoresis to recover a 2.6 kb DNA fragment. This fragment strongly hybridized to the probe. It was subcloned to a plasmid vector pBLUESCRIPT (Stratagene) to give a plasmid pBB2.6.

Experimental Example 2 Isolation of the Arabidopsis ATase cDNA (1) Construction of a cDNA library Total RNA was prepared from about 15 g (wet weight) of leaves and stems of *Arabidopsis thaliana* Heynhold (Lansberg strain) according to the method described in *Current Protocols in Molecular Biology* (Ausbel, F. M. et al. eds.) vol. 1, pp. 4,3,1–4,3,4, John Wiley and Sons, 1987. Poly(A)⁺ RNA was prepared from the total RNA according to Wolf et al. (Nucleic Acids Res., 15:2911, 1987).

DNA complementary to the above poly(A)⁺ RNA was synthesized according to the manual of a cDNA synthesis kit purchased from Pharmacia (Code No. 27- 9260-01), using an oligo(dT) nucleotide as a primer. An EcoRI adapter containing a NotI recognition sequence (Pharmacia) was ligated at each terminus of the double strand cDNA thus synthesized, which was followed by ligation to the EcoRI site of a λ phage vector λZAPII (Stratagene). The phage DNA was packaged in vitro using an in vitro packaging kit (GIGAPACK H GOLD: Stratagene) to give a cDNA library in λZAPII.

(2) Isolation of the ATase cDNA

*Escherichia coil* strain XL1-Blue (Stratagene) was infected by the λ phage library, and five plates (10 cm×14 cm) with 2×10⁴ plaques each were screened. The phages were transferred to filters, which were incubated at 65° C. for 1 hour in a hybridization solution containing 6×SSC, 0.05% skim milk and 0.02% sodium azide. A fragment of the genomic ATase gene of Arabidopsis was obtained by excising, with a restriction enzyme BamHI, from the recombinant plasmid pBB2.6 carrying a fragment of the Arabidopsis ATase gene (Experimental example 1(2)). This DNA fragment was subjected to nick translation (nick translation kit, Takara Shuzo) with $^{32}$P-dATP to give a probe with a specific activity of about $10^7$ dpm/µg.

The probe was added to the hybridization solution and the filters were further incubated in this solution at 65° C. for 16 hours. The filters were then washed at 65 ° C. with 1×SSC and 0.1% SDS solution and subjected to autoradiography to select phages which hybridized strongly to the probe.

Inserts were excised from the phage DNAs with a restriction enzyme EcoRI and subjected to 1% agarose gel electrophoresis to determine the size of the fragments. One of the DNA fragments was about 1.4 kb. This fragment was subcloned in a plasmid vector pBLUESCRIPT (Stratagene) to give a plasmid pARAT. The nucleotide sequence of the fragment was determined by the dideoxy termination method (*Proc. Natl. Acad. Sci. USA* 84:4767, 1987).

The insert was 1,445 bp in length with an open reading frame of 1,380 bp (with a stop codon), which is shown in the sequence listing as SEQ ID NO: 1. In consideration of a high homology of the open reading frame to the squash ATase cDNA in both the nucleotide and amino acid sequences, it was deduced that the DNA sequence from nucleotide 16 to 1392 of SEQ ID NO: 1 encodes the precursor of the Arabidopsis ATase (SEQ ID No: 2) containing a transit peptide to chloroplasts, consisting of 459 amino acids with a molecular mass of 50,431. Non-coding regions of 15 bp and 53 bp were present at the upstream and downstream of the open reading frame, respectively. The amino acid sequence –90 to –1 in SEQ ID NO: 2 is presumably a transit peptide to chloroplasts by comparison with the squash ATase.

Experimental Example 3 Expression of the ATase genes of Arabidopsis and squash (control) in *E. coil* and the comparison of their substrate selectivities (1) Construction of *E. coil* expression vectors The plasmid pARAT obtained in Experimental Example 2(2) was digested with restriction enzymes HgaI, which cuts after nucleotide 285 of SEQ ID NO: 1, and EcoRI (the restriction site for which is in the vector sequence downstream of the cDNA). The resulting 1.1 kb fragment containing the Arabidopsis ATase cDNA was isolated from a low melting agarose gel and made blunt-ended with the Klenow fragment. Meanwhile, plasmid pET3c (Novagen) was digested with a restriction enzyme BamHI and made blunt-ended with the Klenow fragment, and then the phosphoryl group at 5'-terminus was removed with bacterial alkaline phosphatase. The cDNA fragment of the Arabidopsis ATase and pEF3c thus obtained were ligated by T4 DNA ligase to give an expression vector plasmid pAR1 containing a T7 promoter, a T7 leader sequence, the ATase cDNA of Arabidopsis, and a T7 terminator.

Plasmid pAT-03 containing a cDNA for the squash ATase was prepared from *E. coli* AT-03 CFERM BP-3094), digested with restriction enzymes EcoRI and NaeI and then subjected to an electrophoresis on a low melting agarose gel to isolate a 1.2 kb cDNA fragment of the squash ATase. This fragment was made blunt-ended with the Klenow fragment and the phosphoryl group at 5'-terminus was removed with bacterial alkaline phosphatase. The cDNA fragment of the squash ATase and pET3c thus obtained were ligated by T4 DNA ligase to give an expression vector plasmid pSQ1 containing a T7 promoter, a T7 leader sequence, the ATase cDNA of squash and a T7 terminator.

Competent cells of *Escherichia coil* BL21 (DE3) (Novagen) were prepared as described in *Molecular Cloning* (Maniatis, T. et al. eds.), pp. 250–251, 1982. Either of the plasmid pAR1 or pSQ1 obtained above was introduced into competent cells, and selection with ampicillin gave transformants BLAR1 and BLSQ1, respectively.

The transformants BLAR1 and BLSQ1 were each inoculated into 500 ml of the LB medium (containing 200 µg/ml of ampicillin) and cultured at 37° C. Cells were grown until the turbidity of the culture reached 0.5OD. at a wavelength of 600 nm. Then isopropyl-thio-galactoside was added to a final concentration of 0.4 mM, and the culture was continued for 3 hours to induce the expression of the ATase protein. Bacterial cells were collected from the culture by centrifugation at 14,000 g for 10 minutes. The pellets were rinsed with 50 mM Tris-HCl (pH 7.4) and resuspended in HM buffer [45 mM Tris-HCl, pH 7.4, 2 mM DTT, 10% glycerol, 10 mM sodium ascorbate, 1 mM benzamidine-HCl, 10 µg/ml leupeptin, 5 mM 6-aminohexanoic acid]. The bacterial suspension was passed through a French pressure cell at 10,000 psi to break the cells. The homogenate was centrifuged at 16,000 g for 10 minutes and further at 100,000 g for 60 minutes, and the supernatant was recovered as a crude enzyme fraction. The etude enzyme fraction was subjected to SDS electrophoresis on a 10% polyacrylamide gel and stained with Coomassie-Brilliant Blue to detect the ATase of Arabidopsis or squash as a protein with a relative molecular mass of about 40,000.

(2) Assay of the ATase activity

The ATase activity of the crude enzyme fractions prepared above was assayed by the method of Nishida et al. (*Plant Cell Physiol.*, 28:1071, 1987) using 16:0-CoA and L-[U-$^{14}$C] glycerol 3-phosphate as the substrates. Both of the crude enzyme fractions from the *E. coli* transformants BLAR1 and BLSQ1 exhibited the ATase activity (the transfer of 16:0 to glycerol 3-phosphate). The specific activities of ATase in the fractions were 2,000 and 530 nmol/min. mg protein, respectively.

The substrate selectivity of the ATase activity thus obtained was analyzed according to Frentzen et al. (*Plant Cell Physiol.* 28:1195, 1987). The reaction mixture contained 30 mM of glycerol 3-phosphate, 1.5 µM each of [1-$^{14}$C] 16:0-ACP and [1-$^{14}$C] 18:1-ACP, and the crude enzyme fraction of the expressed ATase corresponding to the enzyme activity of about 180 pmol/min. The selectivity was assayed at pH 7.4 and 8.2. The results are shown in Table 1. The expressed Arabidopsis ATase, in contrast to the expressed squash ATase, showed a high selectivity for 18:1-ACP.

TABLE 1

Substrate selectivity of ATases expressed in *E. coli*

| Source of cDNA | Incorporation into lyso-phosphatidic acid* 18:1/16:0 | |
|---|---|---|
| | pH 7.4 | pH 8.2 |
| Arabidopsis | 73/27 | 65/35 |
| Squash | 68/32 | 56/44 |

*under the presence of 30 mM glycerol 3-phophate, 1.5 µM [1-$^{14}$C] 18:1-ACP and 1.5 µM [1-$^{14}$C] 16:0-ACP.

EXAMPLE 1 Expression of the cDNA for Arabidopsis ATase in transgenic tobacco

Tobacco is a chilling-sensitive plant, but relatively chilling-resistant among sensitive plants. The cDNA for the Arabidopsis ATase was introduced and expressed in transgenic tobacco plants as follows.

(1) Construction of a plant expression vector

A plant binary expression plasmid pBI121 (Clontech) was digested with restriction enzymes SacI and BamHI, made blunt-ended with the Klenow fragment, and ligated with T4 DNA ligase. Plasmid pBI121(-GUS) thus obtained has the β-glucuronidase (GUS) gene deleted. This plasmid has unique cloning sites of XbaI and BamHI between the cauliflower mosaic virus 35S promoter (hereinafter called 35S promoter) and the nopaline synthase (NOS) terminator.

Plasmid pARAT, obtained in Experimental Example 2, was digested with EcoRI, and the 1.4 kb Arabidopsis ATase cDNA fragment and the vector fragment were separated by a low-melting-point agarose gel electrophoresis. The cDNA fragment was excised from the gel, purified, and was filed-in with the Klenow fragment. The cDNA fragment was cloned into the filled-in XbaI site of pBI121(-GUS) obtained above to construct an expression plasmid pBI121-35SART, which carries the Arabidopsis ATase cDNA under the control of the 35S promoter and the NOS terminator.

(2) Introduction of pBI121-35SART into Agrobacterium

*Agrobacterium tumefaciens* LBA4404 (Clontech) was inoculated into 50 ml of YEB medium [beef extract 5 g/l, yeast extract 1 g/l, peptone 1 gA, sucrose 5 g/l 2 mM MgSO$_4$, pH 7.4] and harvested after a 24 hr culturing at 28° C. by centrifuging at 3,000 rpm, 4° C. for 20 minutes. The cells were washed three times with 10 ml of 1 mM HEPES (pH 7.4), washed once with 3 ml of 10% glycerol, and suspended in 3 ml of 10% glycerol to be used in the following experiment.

50 µl of the Agrobacterium suspension and 1 µg of the plasmid pBI121- 35SART were put into a cuvette and subjected to an electric pulse using Gene Pulser electroporator (Bio-Rad) under the condition of 25 µF, 2,500 V, 200 Ω to introduce the plasmid into the bacteria. The electropointed suspension was transferred to an Eppendorf tube and 800 µl of SOC medium [triptone 20 g/l, yeast extract 5 g/l, NaCl 0.5 g/l, 2.5 mM KCl, pH 7.0] was added, and the robe was kept at 28° C. for 1.5 hours. 50 µl of the bacterial suspension was spread onto a YEB plate (agar 1.2%) containing 100 ppm of kanamycin and incubated at 28° C. for 2 days.

A single colony was picked up from the colonies formed on the plate. The colony was cultured in a mall scale and the plasmid DNA was isolated by the alkaline method. The plasmid DNA was digested with appropriate restriction enzymes, separated on a 1% agarose gel, and the presence of pBI121-35SART was confirmed by Southern blotting analyses using a $^{32}$P-labelled Arabidopsis ATase cDNA fragment as the probe. This Agrobacterium was termed ALBSART.

(3) Transformation of tobacco

ALBSART was cultured in LB liquid medium containing 50 ppm of kanamycin for 12 hours at 28° C. Cells were harvested from a 1.5 ml portion of the culture by centrifuging at 10,000 rpm for 3 minutes, washed with 1 ml of LB medium to remove kanamycin, and was suspended in 1.5 ml of LB medium to be used in the following experiment.

Young tobacco leaves were immersed in 0.5% NaClO for 10 minutes, washed three times with sterile water, and excess water was wiped off with sterile filter paper. The leaves were aseptically cut into 1 cm$^2$ pieces and floated on the ALBSART suspension with the reverse side up for 2 minutes with mild shaking, and excess bacterium suspension was wiped off on sterile filter paper. 1 ml of a tomato suspension culture (cultivar "Kurikoma") was spread on a MS-B5 plate [MS medium containing benzyladenine 1.0 ppm, naphthalene acetate 0.1 ppm, agar 0.8%] (Murashige, T. and Skoog, F. S., *Plant Physiol.*, 15:473, 1962). A piece of Whatman No. 1 filter paper (φ7 cm) was put on the tomato suspension culture, and the tobacco leaf pieces were put on the filter paper with the reverse side up. The plate was sealed with Parafilm® and incubated at 25° C. for two days under 16 hour light/8 hour dark condition (except otherwise described, the tobacco explants/plants were incubated under this condition). The leaves were transferred to a MS-B5 plate containing 250 ppm Claforan (Hoechst) and further incubated for 10 days to eliminate Agrobacteria. The leaves were then put on MS-B5 medium containing 250 ppm Claforan and 100 ppm kanaxnycin and incubated for 7 days, during which period the rim of the leaf pieces formed callus and shoot primodiums. After another 10 days of incubation, the elongated shoots were transferred to MS hormone free medium containing 250 ppm Claforan and 100 ppm kanamycin. Shoots that rooted on this medium within 10 days of incubation were picked up as kanamycin-resistant transformants and transferred to MS hormone free medium containing 250 ppm Claforan in transparent plastic containers.

(4) Western blot analyses of the transformed tobacco plants 0.5 g (wet weight) of tobacco leaf samples were homogenized with mortar and pestle in an extraction buffer containing 80 mM Tris-HCl (pH 6.8), 2% SDS, 5% glycerol, and 720 mM 2-mercaptoethanol. The homogenate was transferred to an Eppendorf tube and heated at 100° C. for three minutes, after which the supernatant was recovered by a centrifugation at 15,000 rpm, 20° C. for 10 minutes to obtain a crude total protein extract. The protein concentration was measured using a protein assay kit (Bio-Rad) and adjusted to 1 μg/μl.

10 μl of the total protein extract was mixed with the sample loading buffer and electophoressed in an SDS-PAGE gel (Daiichi-kagaku Co.) according to Laemmli (*Nature*, 227:680, 1970). The proteins were blotted onto a PVDF membrane filter (Millipore) using an electroblotting apparatus (Atto) in a blotting buffer containing 0.025 M Tris, 0.192 M glycine, 20% ethanol and 0.01% SDS at 100 V for one hour.

The membrane was immersed in the milk solution [5% skim milk (Difco), 10 mM Tris-HCl, 150 mM NaCl, 0.05% Tween-20, 0.05% $NAN_3$, pH 7.2] and washed by shaking at room temperature for 3×10 minutes. It was further incubated in the milk solution at room temperature for three hours to block the non-specific absorption of the antibody and then washed by shaking for 2×3 minutes in TBS-T buffer [10 mM Tris-HCl, 150 mM NaCl, 0.05% Tween-20, 0.05% $NaN_3$, pH 7.2].

The membrane was incubated in an anti-(Arabidopsis ATase) mouse antiserum diluted 500-fold with TBS-T buffer with shaking at room temperature for two hours, followed by washing in the milk solution for 3×10 minutes and in TBS-T buffer for 2×3 minutes at room temperature. Proteins reacted with the antibody were visualized by the peroxidase staining using Vectastain ABC kit (Vector Laboratories) according to the supplier's instruction.

The total proteins extracted from transformed tobacco plants contained a protein reactive with the antibody against Arabidopsis ATase in an amount of approximately 0.5% of the total proteins.

EXAMPLE 2 Fatty acid composition of phosphatidylglycerol from the leaves of transgenic tobacco Phosphatidylglycerol (PG) was extracted from the leaves of transgenic tobacco plants obtained above and control non-transformed tobacco plants to analyze the fatty acid composition.

(1) Extraction of total lipids

Total lipids were extracted according to Bligh and Dyer (Can. *J. Biochem. Physiol.*, 37:911, 1959). 2 g (wet weight) of leaf samples were cut into strips using a scalpel and put quickly into 5 ml of pre-heated (80° C.) isopropanol containing 0.1% butylhydroxytoluene, kept at 80° C. for 5 minutes, and cooled to room temperature. 20 ml of chloroform:methanol (1:2 v/v) was added and the leaves were homogenized with a homogenizer and let stand for 15 minutes. 12 ml each of chloroform and distilled water were added and the mixture was vigorously shaken and then centrifuged at 3,000 rpm, 4° C. for 30 minutes to separate it into aqueous and organic layers. The organic (bottom) layer was recovered and, after adding an appropriate amount of ethanol, evaporated to dryness under reduced pressure at 30 ° C. using a rotary evaporator. Total lipids thus obtained were dissolved in 2 ml of chloroform:methanol (1:4, v/v).

(2) Fractionation of lipid classes 25 ml suspension of DEAE-Toyopearl (Toso) was mixed with 25 ml of 1 M sodium acetate (pH 7.0) to activate the resin. It was then washed with distilled water, methanol, suspended in methanol and packed in a column ($\phi$2 cm) to a height of 1.5 cm. The column was washed with 50 ml of chloroform:methanol (1:4, v/v).

The total lipids were loaded onto the column. First, monogalactosyldiacytglycerol, digalactosyidiacylglycerol, phosphatidylethanolamine and phosphatidylcholine were eluted out with 50 ml of chloroform:methanol (1:4, v/v). Second, phosphatidylserine was eluted out with 5 ml of acetic acid. Finally, PG, sulfoquinovosyldiacylglycerol and phosphatidylinositol were eluted with 50 ml of chloroform:methanol:10 M aqueous ammonium acetate (20:80:0.2, v/v). After adding 15 ml of ethanol, the last fraction was evaporated under reduced pressure and the residue was dissolved in 1 ml of chloroform:methanol (2:1, v/v).

PG was purified from the fractionated lipids by TLC on a silica gel plate (Merck #5721) using chloroform:acetone:methanol:acetic acid:water (50:20:10:15:5, v/v) as the developing solvent. The lipids were visualized by primulin fluorescence and PG was identified by comparing the migration rate with a standard PG preparation.

(3) Fatty acid analysis

Silica powder containing the PG was scraped off from the TLC plate and put into a screw-capped test robe. 2.5 ml of 5% HCl/methanol was added to the tube and the lipid was methanolyzed at 85° C. for 2.5 hours in the robe tightly capped. The resultant fatty acid methyl esters were extracted four times with 5 ml of hexane, combined and concentrated under reduced pressure, and analyzed by gas chromatography. Fatty acids were identified by comparing the retention time with standard fatty acid methyl esters and quantified with Shimadzu Chromatopack C-R 2AX. The results are shown in Table 2.

While the content of saturated fatty acids (16:0+16:1t+ stearic acid (18:0)) in PG was 68=1% in the control non-transformed plants, it was decreased to 63±1 % in the transgenic plants expressing the Arabidopsis ATase. Considering that the sn-2 position of PG is occupied exclusively by 16:0 and 16:1t, the content of saturated molecular species in PG is calculated from the fatty acid content to be 36±1% for non-transformed plants and 26±1% for transgenic plants (Table 2).

No significant difference was observed between the control and the transgenic plants in the fatty acid compositions of major lipid classes other than PG.

TABLE 2

Fatty acid and molecular species compositions in PG

| Plant | 16:0 + 16:1t + 18:0 | Saturated molecular species |
|---|---|---|
| Non-transformed tobacco | 68 ± 1% | 36 ± 1% |
| Arabidopsis | 60 ± 1% | 20 ± 2% |
| Transgenic tobacco | 63 ± 1% | 26 ± 1% |

EXAMPLE 3 Transport of the expressed Arabidopsis ATase to chloroplasts

Intact chloroplasts were prepared from the transgenic tobacco of Example 1 and control non-transformed tobacco plants and the chloroplast proteins were analyzed.

(1) Preparation of intact chloroplasts 10 g (wet weight) of leaf samples were chopped with scissors and quickly put into 30 ml of ice-cold homogenizing buffer [50 mM sodium pyrophosphate, 1 mM $MgCl_2$, 1 mM EDTA. 2Na, 2 mM sodium isoascorbate, 0.1% bovine serum albumin. 330 mM sorbitol, pH 7.8]. The leaves were mildly broken by a Polytron® and filtered through four layers of Milacloth. The filtrate was centrifuged at 2,000 g, 4° C. for 2 minutes to recover the pellet, which was completely suspended in 3 ml of suspension buffer [50 mM HEPES-NaOH, 330 mM sorbitol, pH 7.6] using a brush. Cell debris were removed by a centrifugation at 100 g, 4° C. for 2 minutes and the chloroplast fraction were recovered by centrifuging at 2,000 g, 4° C. for 2 minutes. The pellet was completely re-suspended in 1 ml of the suspension buffer using a brush.

A tube of Percoll® gradient (from bottom to top: 80% 2.6 ml, 40% 12 ml. 15% 5.4 ml) was prepared at 4° C. and let stand for a while. The chloroplast suspension was loaded onto the gradient and centrifuged at 7,000 g, 4° C. for 15 minutes. Intact chloroplasts were separated at the interface between 80% and 40% Percoll as a green band, which was washed with five volumes of the suspension buffer and recovered by centrifuging at 2,000 g, 4° C. for 5 minutes.

(2) Analysis of the total chloroplast proteins

The intact chloroplasts were suspended in 400 µl of the extraction buffer and the total chloroplast proteins were extracted in the same way as described in Example 1(4). 10 µg of the total chloroplast proteins were subjected to the Western blot analysis as described in Example 1(4). The result is shown in FIG. 1.

A band corresponding to the Arabidopsis ATase, which reacted with the antibody against Arabidopsis ATase, was detected in the total chloroplast protein preparations from transgenic tobacco plants. This indicates that the Arabidopsis ATase expressed in the transgenic tobacco plants was transported to tobacco chloroplasts.

Furthermore, a soluble protein fraction was prepared from the intact chloroplasts of transgenic plants and analyzed by Western blotting. A band corresponding to the Arabidopsis ATase, which reacted with the antibody against Arabidopsis ATase, was detected in the soluble chloroplast protein preparation (not shown), which indicates that the transported Arabidopsis ATase was localized in the chloroplast stroma.

EXAMPLE 4 Expression of the squash ATase in tobacco plants

In order to examine in more detail the effect of the saturated molecular species content in PG on the chilling sensitivity of higher plants, the cDNA coding for the squash ATase was introduced and expressed in tobacco plants to obtain transgenic plants containing more saturated PG molecular species than those inherent to tobacco. As is shown in Table 1 of Experimental example 3, the squash ATase does not have a substrate selectivity for 18:1-ACP and transfers both 18:1-ACP and 16:0-ACP in almost the same proportion to the sn-1 position of glycerol 3-phosphate.

The squash ATase cDNA has been cloned by the applicant and its nucleotide sequence is known to public (Ishizaki (Nishizawa), O. et al, FEBS Lett., 238:424, 1988). It can therefore be obtained by any of appropriate methods utilized in the field of genetic engineering, such as chemical DNA synthesis and PCR, according to the sequence information.

When the squash ATase is expressed in transformed tobacco plants, the ATase has to be transported to chloroplasts since it functions there (see Detailed Description of the Invention). To assure this transport, the DNA sequence encoding the transit peptide portion of the Arabidopsis ATase (amino acid −90 to −1 in SEQ ID NO: 2) was fused in frame to the DNA sequence encoding the mature protein of the squash ATase.

pARAT (Experimental example 2(2)) was digested with restriction enzymes HgaI, which curs after nucleotide 285 of SEQ ID NO: 1, and XhoI (the restriction site for which is in the vector sequence upstream of the cDNA). The 320 bp fragment containing the DNA sequence encoding the Arabidopsis transit peptide was isolated and made blunt-ended with the Klenow fragment. Meanwhile the plasmid pAT-03 carrying a squash ATase cDNA (Ishizaki, O. et al, *FEBS Lett.*, 238:424, 1988) was digested with a restriction enzyme EcoRI and the 1.4 kb fragment containing the squash ATase cDNA was isolated, which was inserted into the EcoRI site of pUC19 (Takara Shuzo) to make the plasmid pUC19/AT03. This plasmid was linearized with NaeI and the ends were made blunt with the Klenow fragment.

The two DNA fragments were ligated together with T4 DNA ligase and a plasmid having one transit peptide DNA fragment inserted in a correct orientation with the squash ATase cDNA was selected, which was termed pSQAR. pSQAR codes for, from 5' to 3', (most likely a part of) squash ATase transit peptide and the Arabidopsis ATase transit peptide fused in frame to the mature squash ATase, between which are the multi-cloning sites derived from pARAT. The fusion protein would be processed to a protein identical to the mature squash ATase except for the substitution of Leu for Pro at the second position from the N-terminus upon expression and transportation to chloroplasts in transgenic plants.

An EcoRI fragment encoding the fusion protein was excised from pSQAR, made blunt-ended with the Klenow fragment, and inserted into the SmaI site of the plant transformation vector pBI121 (Clontech) to obtain pBI121-35SSQAR. This vector plasmid carries the DNA sequence encoding the fusion protein under the control of the 35S promoter and the NOS terminator, with the structural gone for GUS inserted between the fusion protein region and the terminator.

Tobacco was transformed with pBI121-25SSQAR as described in Example 1(2) and (3) to obtain transgenic tobacco plants expressing the squash ATase. PG samples were enacted from the leaves of the transgenic plants and their fatty acid compositions were analyzed as in Example 2. The content of saturated fatty acids (16:0+16:1t+18:0) was 72±1% and the saturated molecular species content was calculated to be 44%. This value was higher than the value of 36% for the non-transformed tobacco (see Table 2) indicating the fatty acid composition of PG from the transgenic tobacco was shifted to a chilling-sensitive type. For comparison, PG from squash leaves contain 64% saturated molecular species.

EXAMPLE 5 Effects of a low temperature treatment on the photosynthetic activities of transgenic tobacco leaves Photosynthesis is one of the most dominant and important biochemical processes in higher plants, and the loss of its activity leads to the damage of physiological activity of the whole plant. The loss of photosynthetic activity by a low temperature treatment is therefore a good indication of the chilling sensitivity of the plant.

Accordingly, photosynthetic oxygen evolution of leaves was compared before and after a low temperature treatment for the transgenic tobacco plants of Examples 1 and 4, as well as those transformed with the vector pBI121.

Figure 2:
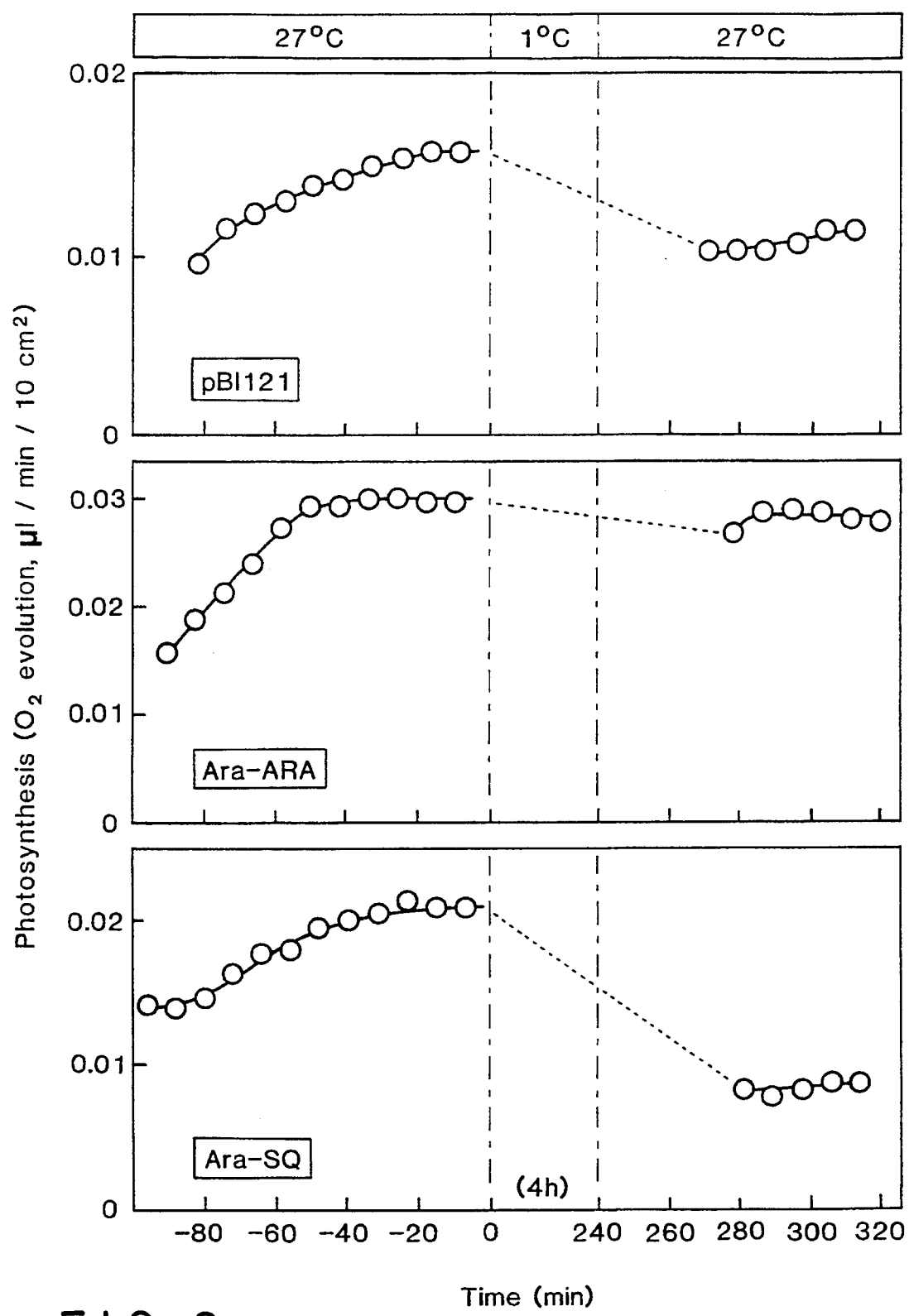
FIG. 2 shows the effect of a chilling treatment on the photosynthetic activity of transgenic tobacco plants. From top to bottom: tobacco transformed with the vector pBI121, the Arabidopsis ATase cDNA and the squash ATase cDNA.
Figure 3B:
Figure 3B:
Figure 3D:
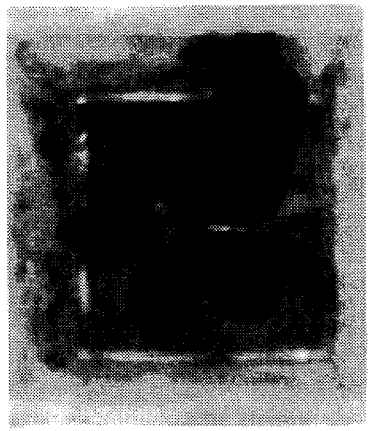
Figure 3D:
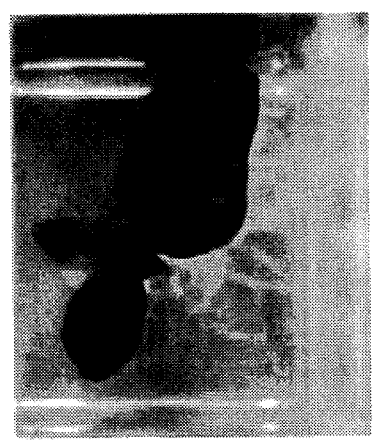

Oxygen evolution of leaves was measured with a Clark-type oxygen electrode assembled for the gas-phase measurement. A 8.5–10 cm$^2$ leaf disk was cut from an intact leaf and placed on a wetted sponge mat in the temperature-controlled chamber of the leaf disk electrode unit (Hanzatech, LD2). White light from a 100 W tungsten lamp (Hanzatech, LS2) passed through a heat-cut off filter (Hoya, HA-50) was used as the actinic light for photosynthetic oxygen evolution (1,000 μE/m$^2$/sec). The gas phase of the chamber was replaced with air containing 5% $CO_2$ every 7 minutes. Oxygen evolution from the leaf disk was measured at 27° C. continuously for about 90 minutes, then the temperature of the chamber was lowered to 1° C. The leaf disk was kept at this low temperature under the same illumination for 4 hours, after which the temperature was raised again to 27° C. and oxygen evolution was measured as above. FIG. 2 shows the results obtained with the transgenic tobacco of Examples I and 4, and the control tobacco transformed with the vector pBI121, which is identical to non-transformed tobacco with respect to chilling sensitivity.

In both measurements before and after the chilling treatment, the oxygen evolution activities gradually increased to reach a plateau after some time. The activities at that time were taken as the activities before and after the treatment, respectively, and their ratio was calculated as an indicator of the chilling sensitivity as shown in Table 3.

TABLE 3

| Damage of photosynthesis at 1° C. in transgenic tobacco plants | |
| --- | --- |
| Tobacco plant transformed with | Activity after treatment at 1° C. (relative to that before treatment) |
| pBI121 | |
| #1 | 0.86 |
| #2 | 0.70 |
| #3 | 0.73 |
| Arabidopsis ATase cDNA | |
| #1 | 0.91 |
| #2 | 0.96 |
| #3 | 0.93 |
| #4 | 0.90 |
| Squash ATase cDNA | |
| #1 | 0.53 |
| #2 | 0.41 |

While the photosynthetic oxygen evolution activity of the control pBI121 transformed plants decreased to 70–86% of the original level by low temperature treatment at 1° C. for 4 hours, that of the Arabidopsis ATase transgenic plants little decreased and retained 90–96% of the original level after the treatment. This shows that the photosynthetic oxygen evolution activity of the Arabidopsis ATase transgenic plants is more resistant to low temperature than the control. It is thus concluded that the Arabidopsis ATase transgenic plants are more chilling-resistant than the control.

On the other hand, the photosynthetic oxygen evolution activity of the squash ATase transgenic plants decreased to 41–53% of the original level by low temperature treatment at 1° C. for 4 hours, which decrease is significantly larger than the control indicating that the squash ATase transgenic plants become more chilling-sensitive than the control.

EXAMPLE 6 Effects of a low temperature treatment on transgenic tobacco plants

The effects of a low temperature treatment on the whole plant of the transgenic tobacco plants of Example 1 and control non-transformed and pBI121-transformed tobacco plants were examined.

The tobacco plants were grown in vitro in transparent plastic containers. Upper parts of the plants thus grown were cut and each transferred onto MS hormone free medium containing 250 ppm of Claforan in the plastic containers and grown for two weeks at 25° C. under 16 h light/8 h dark condition. Within that period the explants rooted and developed into plantlets with three to four fully expanded leaves.

The tobacco plants in the container were put into a growth chamber (Koito Kogyo Co.: KPS-2000) set at a temperature of 1° C. and kept there for 10 days under a fluorescent lamp illumination of 100 μE/m$^2$/sec. The plants were then transferred to 25° C. (16 h light/8 h dark) for two days and chilling injuries on the plants were observed. FIGS. 3A–3D show one of the transgenic tobacco plants expressing the Arabidopsis ATase and a control pBI121-transformed tobacco before and after the chilling treatment.

pBI121-transformed tobacco plants, as well as non-transformed plants, developed white spots on their leaves after the chilling treatment, which results from the decay of chloroplasts (ehlorosis) by the treatment (FIGS. 3A–3D, upper plate). On the other hand, the Arabidopsis ATase transgenic plants suffered little damage by the treatment (FIG. 3, lower plates) indicating that they are more chilling-resistant than the control plants.

The above Examples conclusively demonstrate application of the present invention to the engineering of chilling resistance into a chilling-sensitive higher plant by introducing and expressing an ATase of chilling-resistant plants in the chilling-sensitive plant and thus decreasing the saturated molecular species in its PG. The fact that the tobacco plants engineered to contain a higher amount of saturated PG molecular species were more sensitive to chilling injury further proves the relationship between the chilling sensitivity and the PG molecular species composition, indicating that the process to give chilling resistance to higher plants according to the present invention can be widely applicable to variety of crop plants. This is the first case of plant genetic engineering for chilling resistance, which will invaluably contribute to agricultural production in areas under chilling climate.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1445 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 16..1392

( i x ) FEATURE:
( A ) NAME/KEY: sig_peptide
( B ) LOCATION: 16..285

( i x ) FEATURE:
( A ) NAME/KEY: mat_peptide
( B ) LOCATION: 286..1392

( x i ) SEQUENCE DESCRIPTION: SEQ ID NO:1:

```
ACCAAACACG CTTTA ATG ACT CTC ACG TTT TCC TCC TCC GCC GCA ACC GTT        51
                Met Thr Leu Thr Phe Ser Ser Ser Ala Ala Thr Val
                -90             -85                 -80

GCC GTT GCT GCT GCA ACC GTA ACC TCC TCC GCT AGG GTT CCG GTT TAT        99
Ala Val Ala Ala Ala Thr Val Thr Ser Ser Ala Arg Val Pro Val Tyr
            -75             -70                 -65

CCA CTC GCT TCG TCG ACT CTT CGT GGA TTA GTA TCT TTC AGA TTA ACC       147
Pro Leu Ala Ser Ser Thr Leu Arg Gly Leu Val Ser Phe Arg Leu Thr
        -60             -55                 -50

GCG AAG AAG CTG TTT CTG CCG CCT CTT CGT TCT CGC GGC GGC GTT AGT       195
Ala Lys Lys Leu Phe Leu Pro Pro Leu Arg Ser Arg Gly Gly Val Ser
    -45             -40                 -35

GTG AGA GCC ATG TCT GAG CTA GTT CAA GAT AAA GAA TCG TCC GTC GCG       243
Val Arg Ala Met Ser Glu Leu Val Gln Asp Lys Glu Ser Ser Val Ala
-30             -25                 -20                 -15

GCG AGC ATT GCT TTC AAT GAA GCC GCC GGT GAG ACG CCG AGT GAG CTT       291
Ala Ser Ile Ala Phe Asn Glu Ala Ala Gly Glu Thr Pro Ser Glu Leu
            -10                 -5                      1

AAT CAT TCC CGT ACT TTC TTG GAT GCG CGA AGT GAA CAA GAT CTT TTA       339
Asn His Ser Arg Thr Phe Leu Asp Ala Arg Ser Glu Gln Asp Leu Leu
        5                   10                  15

TCT GGT ATC AAG AAG GAA GCT GAA GCT GGA AGG TTG CCA GCA AAT GTT       387
Ser Gly Ile Lys Lys Glu Ala Glu Ala Gly Arg Leu Pro Ala Asn Val
    20                  25                  30

GCA GCA GGA ATG GAA GAA TTG TAT TGG AAC TAC AAA AAT GCA GTT TTA       435
Ala Ala Gly Met Glu Glu Leu Tyr Trp Asn Tyr Lys Asn Ala Val Leu
35                  40                  45                  50

AGT AGT GGA GCT TCC AGG GCA GAT GAA ACT GTT GTA TCA AAC ATG TCT       483
Ser Ser Gly Ala Ser Arg Ala Asp Glu Thr Val Val Ser Asn Met Ser
            55                  60                  65

GTT GCT TTT GAT CGC ATG CTT CTT GGT GTG GAG GAT CCT TAT ACT TTT       531
Val Ala Phe Asp Arg Met Leu Leu Gly Val Glu Asp Pro Tyr Thr Phe
        70                  75                  80

AAT CCA TAT CAT AAA GCA GTC AGA GAA CCA TTT GAC TAC TAC ATG TTT       579
Asn Pro Tyr His Lys Ala Val Arg Glu Pro Phe Asp Tyr Tyr Met Phe
        85                  90                  95
```

| | | | | | | | | | | | | | | | | |
|---|---|---|---|---|---|---|---|---|---|---|---|---|---|---|---|---|
| GTC | CAT | ACA | TAC | ATC | CGT | CCT | CTT | ATT | GAT | TTC | AAA | AAT | TCG | TAC | GTT | 627 |
| Val | His | Thr | Tyr | Ile | Arg | Pro | Leu | Ile | Asp | Phe | Lys | Asn | Ser | Tyr | Val | |
| | 100 | | | | 105 | | | | | 110 | | | | | | |
| GGA | AAT | GCT | TCT | ATA | TTC | TCT | GAG | CTG | GAA | GAC | AAG | ATT | CGA | CAG | GGA | 675 |
| Gly | Asn | Ala | Ser | Ile | Phe | Ser | Glu | Leu | Glu | Asp | Lys | Ile | Arg | Gln | Gly | |
| 115 | | | | | 120 | | | | | 125 | | | | | 130 | |
| CAC | AAT | ATC | GTG | TTG | ATA | TCA | AAC | CAT | CAA | AGT | GAA | GCT | GAT | CCG | GCT | 723 |
| His | Asn | Ile | Val | Leu | Ile | Ser | Asn | His | Gln | Ser | Glu | Ala | Asp | Pro | Ala | |
| | | | | 135 | | | | | 140 | | | | | 145 | | |
| GTC | ATT | TCT | CTA | TTG | CTT | GAA | GCA | CAA | TCT | CCT | TTC | ATA | GGA | GAG | AAC | 771 |
| Val | Ile | Ser | Leu | Leu | Leu | Glu | Ala | Gln | Ser | Pro | Phe | Ile | Gly | Glu | Asn | |
| | | | 150 | | | | | 155 | | | | | 160 | | | |
| ATT | AAA | TGT | GTG | GCT | GGT | GAT | CGA | GTC | ATC | ACT | GAT | CCT | CTT | TGT | AAG | 819 |
| Ile | Lys | Cys | Val | Ala | Gly | Asp | Arg | Val | Ile | Thr | Asp | Pro | Leu | Cys | Lys | |
| | | 165 | | | | | 170 | | | | | 175 | | | | |
| CCG | TTC | AGT | ATG | GGA | AGG | AAC | CTC | ATA | TGT | GTT | TAC | TCG | AAA | AAG | CAC | 867 |
| Pro | Phe | Ser | Met | Gly | Arg | Asn | Leu | Ile | Cys | Val | Tyr | Ser | Lys | Lys | His | |
| | | 180 | | | | | 185 | | | | | 190 | | | | |
| ATG | AAT | GTT | GAT | CCT | GAG | CTT | GTT | GAC | ATG | AAA | AGA | AAA | GCA | AAC | ACA | 915 |
| Met | Asn | Val | Asp | Pro | Glu | Leu | Val | Asp | Met | Lys | Arg | Lys | Ala | Asn | Thr | |
| 195 | | | | | 200 | | | | | 205 | | | | | 210 | |
| CGA | AGC | TTA | AAG | GAG | ATG | GCT | ACA | ATG | CTA | AGG | TCT | GGC | GGT | CAA | CTT | 963 |
| Arg | Ser | Leu | Lys | Glu | Met | Ala | Thr | Met | Leu | Arg | Ser | Gly | Gly | Gln | Leu | |
| | | | | 215 | | | | | 220 | | | | | 225 | | |
| ATA | TGG | ATT | GCA | CCA | AGC | GGT | GGA | AGG | GAC | CGC | CCG | AAT | CCT | TCT | ACT | 1011 |
| Ile | Trp | Ile | Ala | Pro | Ser | Gly | Gly | Arg | Asp | Arg | Pro | Asn | Pro | Ser | Thr | |
| | | | 230 | | | | | 235 | | | | | 240 | | | |
| GGG | GAA | TGG | TTT | CCT | GCA | CCC | TTT | GAT | GCT | TCT | TCG | GTA | GAC | AAC | ATG | 1059 |
| Gly | Glu | Trp | Phe | Pro | Ala | Pro | Phe | Asp | Ala | Ser | Ser | Val | Asp | Asn | Met | |
| | | 245 | | | | | 250 | | | | | 255 | | | | |
| AGA | AGA | CTG | GTT | GAA | CAT | TCT | GGC | GCT | CCT | GGA | CAT | ATA | TAT | CCA | ATG | 1107 |
| Arg | Arg | Leu | Val | Glu | His | Ser | Gly | Ala | Pro | Gly | His | Ile | Tyr | Pro | Met | |
| | 260 | | | | | 265 | | | | | 270 | | | | | |
| TCT | TTG | CTT | TGC | TAT | GAC | ATC | ATG | CCC | CCT | CCA | CCC | CAG | GTT | GAG | AAA | 1155 |
| Ser | Leu | Leu | Cys | Tyr | Asp | Ile | Met | Pro | Pro | Pro | Pro | Gln | Val | Glu | Lys | |
| 275 | | | | | 280 | | | | | 285 | | | | | 290 | |
| GAA | ATC | GGA | GAG | AAA | AGA | TTA | GTT | GGG | TTT | CAC | GGT | ACT | GGA | CTA | TCA | 1203 |
| Glu | Ile | Gly | Glu | Lys | Arg | Leu | Val | Gly | Phe | His | Gly | Thr | Gly | Leu | Ser | |
| | | | | 295 | | | | | 300 | | | | | 305 | | |
| ATT | GCT | CCT | GAA | ATC | AAC | TTC | TCA | GAC | GTC | ACA | GCA | GAC | TGC | GAG | AGC | 1251 |
| Ile | Ala | Pro | Glu | Ile | Asn | Phe | Ser | Asp | Val | Thr | Ala | Asp | Cys | Glu | Ser | |
| | | | 310 | | | | | 315 | | | | | 320 | | | |
| CCT | AAT | GAG | GCG | AAA | GAA | GCA | TAC | AGC | CAA | GCT | TTG | TAC | AAG | TCG | GTG | 1299 |
| Pro | Asn | Glu | Ala | Lys | Glu | Ala | Tyr | Ser | Gln | Ala | Leu | Tyr | Lys | Ser | Val | |
| | | 325 | | | | | 330 | | | | | 335 | | | | |
| AAT | GAA | CAA | TAC | GAG | ATC | TTA | AAC | TCT | GCG | ATT | AAA | CAC | AGA | AGA | GGA | 1347 |
| Asn | Glu | Gln | Tyr | Glu | Ile | Leu | Asn | Ser | Ala | Ile | Lys | His | Arg | Arg | Gly | |
| | 340 | | | | | 345 | | | | | 350 | | | | | |
| GTA | GAA | GCA | TCA | ACT | TCA | AGG | GTC | TCT | TTG | TCA | CAA | CCT | TGG | AAT | | 1392 |
| Val | Glu | Ala | Ser | Thr | Ser | Arg | Val | Ser | Leu | Ser | Gln | Pro | Trp | Asn | | |
| 355 | | | | | 360 | | | | | 365 | | | | | | |
| TAGTCTCTCG | TTTAGGGAT | ACACAAACAC | AATCAATGGA | AAATACTCAA | AAA | | | | | | | | | | | 1445 |

( 2 ) INFORMATION FOR SEQ ID NO:2:

( i ) SEQUENCE CHARACTERISTICS:
        ( A ) LENGTH: 459 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Leu  Thr  Phe  Ser  Ser  Ser  Ala  Ala  Thr  Val  Ala  Val  Ala  Ala
-90            -85                      -80                          -75
Ala  Thr  Val  Thr  Ser  Ser  Ala  Arg  Val  Pro  Val  Tyr  Pro  Leu  Ala  Ser
               -70                      -65                          -60
Ser  Thr  Leu  Arg  Gly  Leu  Val  Ser  Phe  Arg  Leu  Thr  Ala  Lys  Lys  Leu
               -55                      -50                     -45
Phe  Leu  Pro  Pro  Leu  Arg  Ser  Arg  Gly  Val  Ser  Val  Arg  Ala  Met
          -40                      -35                     -30
Ser  Glu  Leu  Val  Gln  Asp  Lys  Glu  Ser  Ser  Val  Ala  Ala  Ser  Ile  Ala
     -25                 -20                      -15
Phe  Asn  Glu  Ala  Ala  Gly  Glu  Thr  Pro  Ser  Glu  Leu  Asn  His  Ser  Arg
-10                       -5                      1                         5
Thr  Phe  Leu  Asp  Ala  Arg  Ser  Glu  Gln  Asp  Leu  Leu  Ser  Gly  Ile  Lys
               10                      15                          20
Lys  Glu  Ala  Glu  Ala  Gly  Arg  Leu  Pro  Ala  Asn  Val  Ala  Ala  Gly  Met
          25                      30                          35
Glu  Glu  Leu  Tyr  Trp  Asn  Tyr  Lys  Asn  Ala  Val  Leu  Ser  Ser  Gly  Ala
     40                      45                      50
Ser  Arg  Ala  Asp  Glu  Thr  Val  Val  Ser  Asn  Met  Ser  Val  Ala  Phe  Asp
55                  60                      65                          70
Arg  Met  Leu  Leu  Gly  Val  Glu  Asp  Pro  Tyr  Thr  Phe  Asn  Pro  Tyr  His
               75                      80                          85
Lys  Ala  Val  Arg  Glu  Pro  Phe  Asp  Tyr  Tyr  Met  Phe  Val  His  Thr  Tyr
               90                      95                          100
Ile  Arg  Pro  Leu  Ile  Asp  Phe  Lys  Asn  Ser  Tyr  Val  Gly  Asn  Ala  Ser
          105                     110                     115
Ile  Phe  Ser  Glu  Leu  Glu  Asp  Lys  Ile  Arg  Gln  Gly  His  Asn  Ile  Val
     120                     125                     130
Leu  Ile  Ser  Asn  His  Gln  Ser  Glu  Ala  Asp  Pro  Ala  Val  Ile  Ser  Leu
135                 140                     145                         150
Leu  Leu  Glu  Ala  Gln  Ser  Pro  Phe  Ile  Gly  Glu  Asn  Ile  Lys  Cys  Val
               155                     160                     165
Ala  Gly  Asp  Arg  Val  Ile  Thr  Asp  Pro  Leu  Cys  Lys  Pro  Phe  Ser  Met
               170                     175                     180
Gly  Arg  Asn  Leu  Ile  Cys  Val  Tyr  Ser  Lys  Lys  His  Met  Asn  Val  Asp
          185                     190                     195
Pro  Glu  Leu  Val  Asp  Met  Lys  Arg  Lys  Ala  Asn  Thr  Arg  Ser  Leu  Lys
     200                     205                     210
Glu  Met  Ala  Thr  Met  Leu  Arg  Ser  Gly  Gly  Gln  Leu  Ile  Trp  Ile  Ala
215                 220                     225                         230
Pro  Ser  Gly  Gly  Arg  Asp  Arg  Pro  Asn  Pro  Ser  Thr  Gly  Glu  Trp  Phe
               235                     240                     245
Pro  Ala  Pro  Phe  Asp  Ala  Ser  Ser  Val  Asp  Asn  Met  Arg  Arg  Leu  Val
               250                     255                     260
Glu  His  Ser  Gly  Ala  Pro  Gly  His  Ile  Tyr  Pro  Met  Ser  Leu  Leu  Cys
          265                     270                     275
Tyr  Asp  Ile  Met  Pro  Pro  Pro  Gln  Val  Glu  Lys  Glu  Ile  Gly  Glu
     280                     285                     290
Lys  Arg  Leu  Val  Gly  Phe  His  Gly  Thr  Gly  Leu  Ser  Ile  Ala  Pro  Glu
295                 300                     305                         310
Ile  Asn  Phe  Ser  Asp  Val  Thr  Ala  Asp  Cys  Glu  Ser  Pro  Asn  Glu  Ala
               315                     320                     325
```

| Lys | Glu | Ala | Tyr<br>330 | Ser | Gln | Ala | Leu | Tyr<br>335 | Lys | Ser | Val | Asn | Glu<br>340 | Gln | Tyr |
| Glu | Ile | Leu<br>345 | Asn | Ser | Ala | Ile | Lys<br>350 | His | Arg | Arg | Gly | Val<br>355 | Glu | Ala | Ser |
| Thr | Ser<br>360 | Arg | Val | Ser | Leu | Ser<br>365 | Gln | Pro | Trp | Asn | | | | | |

What is claimed is:

1. A transgenic higher plant characterized by the presence in at least one of its lipid classes of a higher proportion of unsaturated fatty acids than inherently present in species of said plant and by the presence in its cells of an exogenous DNA sequence encoding a polypeptide with a glycerol 3-phosphate acyltransferase activity having a higher substrate selectivity for oleoyl-(acyl-carrier-protein) than for palmitoyl-(acyl-carrier-protein).

2. A transgenic higher plant according to claim 1, wherein the polypeptide is a glycerol 3-phosphate acyltransferase of a chilling-resistant plant.

3. A transgenic higher plant according to claim 2, wherein the chilling-resistant plant is spinach, pea, or Arabidopsis.

4. A process for increasing the unsaturated fatty acid content in lipids of a higher plant species comprising introducing into the cells thereof an exogenous DNA sequence encoding a polypeptide with a glycerol 3-phosphate acyltransferase activity having a higher substrate selectivity for oleoyl-(acyl-carrier-protein) than for palmitoyl-(acyl-carrier-protein).

5. A process according to claim 4, wherein the polypeptide is a glycerol 3-phosphate acyltransferase of a chilling-resistant plant.

6. A process according to claim 5, wherein the chilling-resistant plant is spinach, pea, or Arabidopsis.

7. A transgenic higher plant characterized by having a lowered critical temperature for chilling injury than that inherent in species of said plant and by containing in the biomembranes of its cells a decreased proportion of saturated phosphatidylglycerol molecular species and by the presence in its cells of an exogenous DNA sequence encoding a polypeptide with a glycerol 3-phosphate acyltransferase activity having a higher substrate selectivity for oleoyl-(acyl-carrier-protein) than for palmitoyl-(acyl-carrier-protein).

8. A transgenic higher plant according to claim 7, wherein the polypeptide is a glycerol 3-phosphate acyltransferase of a chilling-resistant plant.

9. A transgenic higher plant according to claim 8, wherein the chilling-resistant plant is spinach, pea, or Arabidopsis.

10. A process for lowering the critical temperature for chilling injury of a higher plant species comprising decreasing the content of saturated phosphatidylglycerol molecular species in the biomembranes of its cells and introducing into its cells an exogenous DNA sequence encoding a polypeptide with a glycerol 3-phosphate acyltransferase activity having a higher substrate selectivity for oleoyl-(acyl-carrier-protein) than for palmitoyl-(acyl-carrier-protein).

11. A process according to claim 10, wherein the polypeptide is a glycerol 3-phosphate acyltransferase of a chilling-resistant plant.

12. A process according to claim 11, wherein the chilling-resistant plant is spinach, pea, or Arabidopsis.

* * * * *